United States Patent
Hirose

(10) Patent No.: US 8,430,509 B2
(45) Date of Patent: Apr. 30, 2013

(54) LIGHT IRRADIATION APPARATUS, ADAPTIVE OPTICS APPARATUS, AND IMAGING APPARATUS INCLUDING THE SAME

(75) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 275 days.

(21) Appl. No.: 12/907,866

(22) Filed: Oct. 19, 2010

(65) Prior Publication Data

US 2011/0102741 A1 May 5, 2011

(30) Foreign Application Priority Data

Oct. 30, 2009 (JP) .................... 2009-251415

(51) Int. Cl.
*A61B 3/14* (2006.01)
*A61B 3/00* (2006.01)

(52) U.S. Cl.
USPC .......................................... 351/206; 351/246

(58) Field of Classification Search ........... 351/200–246
See application file for complete search history.

(56) References Cited

U.S. PATENT DOCUMENTS

| | | | |
|---|---|---|---|
| 4,579,430 A | 4/1986 | Bille | |
| 6,585,724 B2 * | 7/2003 | Toh | .................... 606/5 |
| 7,293,874 B2 * | 11/2007 | Suzuki et al. | ................ 351/208 |
| 7,367,672 B2 | 5/2008 | Akita | |
| 2011/0116044 A1 * | 5/2011 | Nozato et al. | ................ 351/206 |

FOREIGN PATENT DOCUMENTS

| | | |
|---|---|---|
| CN | 1994217 A | 7/2007 |
| EP | 292216 A1 | 11/1988 |
| JP | 2007-014569 A | 1/2007 |
| WO | 2005060823 A1 | 7/2005 |
| WO | 2007023300 A1 | 3/2007 |

OTHER PUBLICATIONS

Enrique J. Fernandez et al., "Three-dimensional adaptive optics ultrahigh-resolution optical coherence tomography using a liquid crystal spatial light modulator", Vision Research 45 (2005) 3432-3444.

* cited by examiner

*Primary Examiner* — Mohammed Hasan
(74) *Attorney, Agent, or Firm* — Canon USA Inc IP Division

(57) ABSTRACT

A light irradiation apparatus includes an optical power acquiring unit configured to acquire an optical power of light emitted by a light source and with which an object is irradiated; an optical power adjusting unit configured to adjust the optical power of light emitted by the light source to a predetermined optical power in accordance with an acquisition result obtained by the optical power acquiring unit; and an irradiation unit configured to irradiate the object with the light that is adjusted by the optical power adjusting unit.

13 Claims, 6 Drawing Sheets

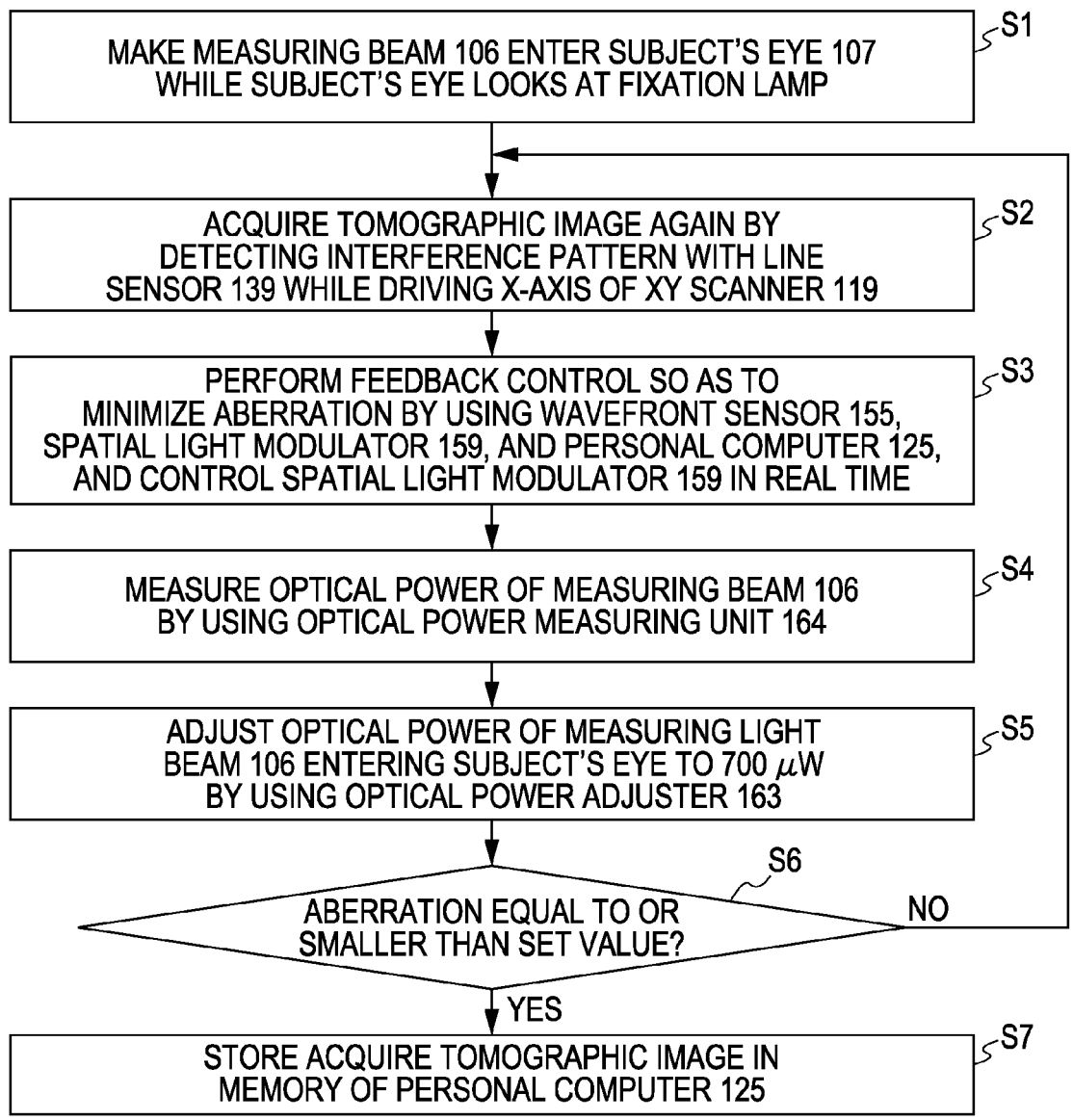

LIGHT IRRADIATION APPARATUS, ADAPTIVE OPTICS APPARATUS, AND IMAGING APPARATUS INCLUDING THE SAME

BACKGROUND OF THE INVENTION

1. Field of the Invention

The present invention relates to a light irradiation apparatus, an adaptive optics apparatus, and an imaging apparatus. In particular, the present invention relates to an imaging apparatus used for ophthalmologic diagnosis and the like.

2. Description of the Related Art

Optical coherence tomography (OCT) using multi-wavelength optical interference is a method of acquiring a high resolution tomographic image of a subject (in particular, an eye ground). Hereinafter, an optical tomographic imaging apparatus that acquires an optical tomographic image by using OCT will be referred to as an OCT apparatus. In recent years, it has become possible to acquire a high-horizontal-resolution tomographic image of a retina by increasing the diameter of the measuring beam used in a Fourier domain OCT apparatus. On the other hand, the increased diameter of the beam diameter of the measuring beam has caused a problem in that, when acquiring a tomographic image of a retina, the signal to noise ratio and the resolution of the tomographic image is decreased due to the aberration generated by the distortion of a curved surface and unevenness of the index of refraction of a subject's eye. To address the problem, an adaptive optics OCT apparatus including an adaptive optics system has been developed. The adaptive optics system measures the aberration of a subject's eye using a wavefront sensor in real time and corrects the aberration using a wavefront correction device, so that a high-horizontal-resolution tomographic image can be acquired.

Japanese Patent Laid-Open No. 2007-14569 describes an ophthalmologic imaging apparatus including such an adaptive optics system. The apparatus is a scanning laser ophthalmoscope (SLO apparatus) that acquires an image of an eye ground by using an adaptive optics system, a liquid crystal spatial phase modulator, a polygon mirror, a galvano mirror, and other components. This ophthalmologic imaging apparatus corrects the aberration generated in a subject's eye by using the liquid crystal spatial phase modulator, thereby preventing the horizontal resolution from decreasing. "Three-dimensional adaptive optics ultrahigh-resolution optical coherence tomography using a liquid crystal spatial light modulator", Vision Research 45 (2005) 3432-3444 describes that a high-resolution tomographic image of an eye ground can be acquired by using an adaptive optics system, a liquid-crystal spatial light modulator, and the like. In this article, a part of aberration that exceeds the maximum modulation amount of a liquid crystal spatial light modulator is corrected by using phase wrapping technology.

SUMMARY OF THE INVENTION

With the ophthalmological apparatus according to Japanese Patent Laid-Open No. 2007-14569 including the adaptive optics system, the aberration of a subject's eye is corrected by using a liquid crystal spatial light modulator, whereby a high-horizontal-resolution image can be acquired. However, Japanese Patent Laid-Open No. 2007-14569 does not described phase wrapping, which is a technology for correcting an aberration that exceeds the maximum modulation amount of the liquid crystal spatial light modulator. On the other hand, although "Three-dimensional adaptive optics ultrahigh-resolution optical coherence tomography using a liquid crystal spatial light modulator", Vision Research 45 (2005) 3432-3444 describes an OCT apparatus that includes an adaptive optics system and corrects the aberration that exceeds the maximum modulation amount of the liquid crystal spatial light modulator by using phase wrapping technology, this article does not describes the reduction in the diffraction efficiency caused by the aberration correction. However, when aberration correction is performed by performing phase wrapping, because the diffraction efficiency of the liquid crystal spatial light modulator is different in accordance with the modulation pattern, the optical power of an incident beam that enters the subject's eye may deviate, so that reduction in the incident optical power may occur. Due to the loss in the incident optical power, the signal to noise ratio of an acquired tomographic image acquire may be reduced.

The present invention provides an optical imaging apparatus and an optical imaging method that, by using an adaptive optics system including a spatial light modulation unit, can make the optical power of a measuring beam be constant irrespective of the modulation pattern and can increase the signal to noise ratio of a tomographic image.

According to an aspect of the present invention, a light irradiation apparatus includes an optical power acquiring unit configured to acquire an optical power of light emitted by a light source and with which an object is irradiated; an optical power adjusting unit configured to adjust the optical power of light emitted by the light source to a predetermined optical power in accordance with an acquisition result obtained by the optical power acquiring unit; and an irradiation unit configured to irradiate the object with the light that is adjusted by the optical power adjusting unit.

According to the present invention, the optical power of the measuring beam can be made constant irrespective of the modulation pattern by using an adaptive optics system including the spatial light modulation unit, whereby an optical imaging apparatus and an optical imaging method that can increase the signal to noise ratio of a tomographic image can be realized.

Further features of the present invention will become apparent from the following description of exemplary embodiments with reference to the attached drawings.

BRIEF DESCRIPTION OF THE DRAWINGS

FIG. 6 is a flowchart illustrating steps of acquiring a tomographic image by using the OCT apparatus according to the second embodiment the present invention.

DESCRIPTION OF THE EMBODIMENTS

Hereinafter, embodiments of the present invention will be described with reference to the drawings. Here, an optical imaging apparatus that is an OCT apparatus that acquires an image of a subject's eye will be described. However, the present invention can be applied to other optical imaging apparatuses such as a scanning laser ophthalmoscope (SLO apparatus).

First Embodiment

An OCT apparatus according to a first embodiment of the present invention will be described. In particular, in the first embodiment, an OCT apparatus including an adaptive optics system that acquires a tomographic image (OCT image) of a subject's eye with high horizontal resolution will be described. The OCT apparatus according to the first embodiment is a Fourier domain OCT apparatus that corrects the aberration of the subject's eye by using a spatial light modulator and acquires a tomographic image of a subject's eye. Such an OCT apparatus can acquire a good tomographic image irrespective of the diopter or the aberration the subject's eye. The OCT apparatus according to the first embodiment includes an optical power adjuster that calculates a loss in the optical power in the spatial light modulator from the spherical power or the cylindrical power of the subject's eye by using a personal computer and controls the optical power of the measuring beam in accordance with the spherical power or the cylindrical power of the subject's eye by using the personal computer. The spatial light modulator is a reflective liquid crystal spatial light modulator that employs the orientation of liquid crystal. As long as the spatial light modulator can modulate the phase of light, materials other than liquid crystal may be used.

Figure 1:
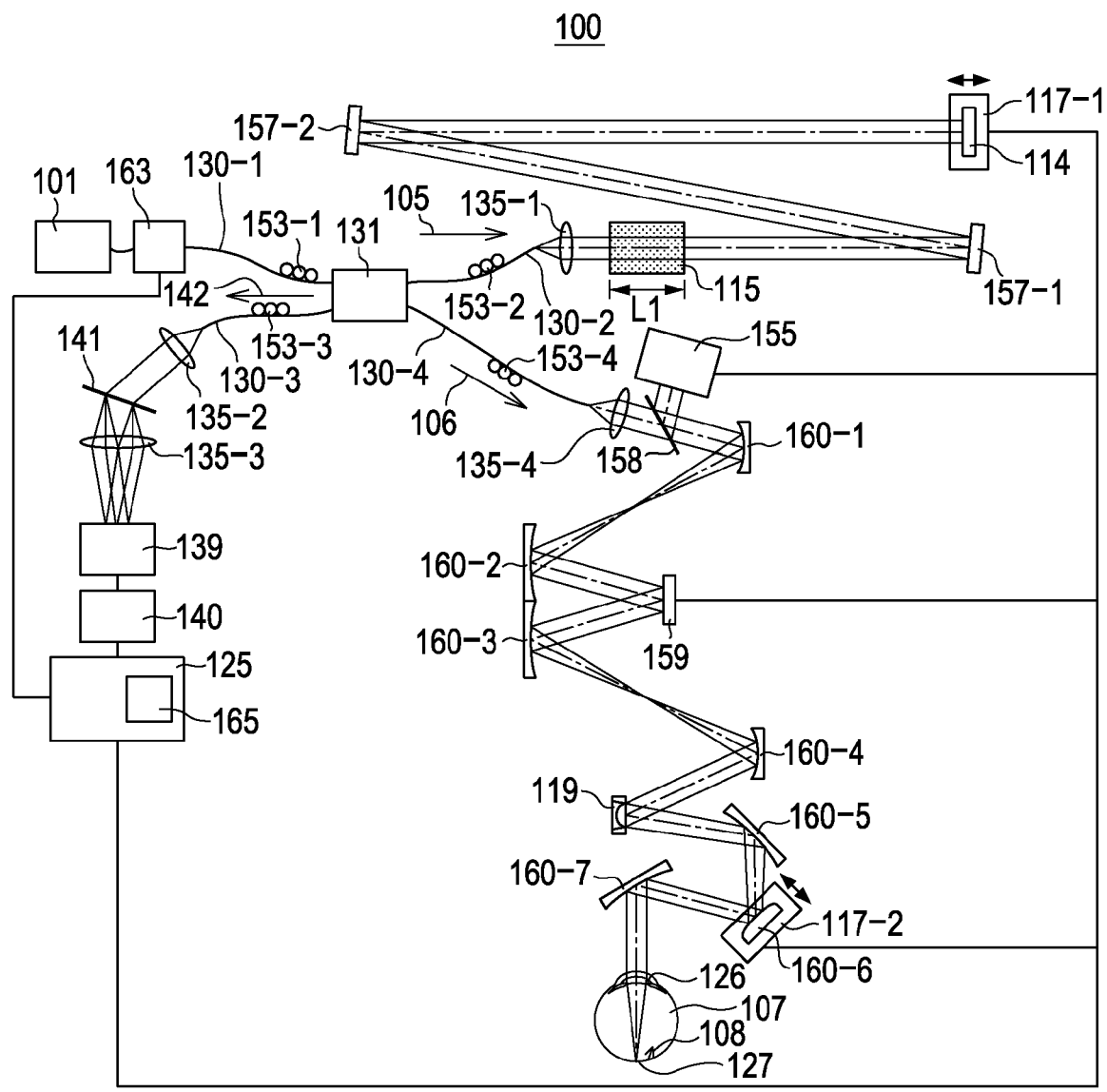
FIG. 1 illustrates the overall structure of an OCT apparatus according to a first embodiment the present invention.

Referring to FIG. 1, the overall structure of the OCT apparatus according to the first embodiment will be described. As illustrated in FIG. 1, the entirety of an OCT apparatus 100 according to the first embodiment is a Michelson interferometer system. In FIG. 1, a light source 101 emits a beam. The beam travels through an optical power adjuster 163, an optical fiber 130-1, and an optical coupler 131, where the beam is split into a reference beam 105 and a measuring beam 106 with a ratio of 90:10. The measuring beam 106 travels through an optical fiber 130-4, a spatial light modulator 159, an XY scanner 119, and spherical mirrors 160-1 to 160-7, and reaches a subject's eye 107 that is an object to be observed.

The measuring beam 106 is reflected or scattered by the subject's eye 107, which is an object to be observed, and returned as a return beam 108. The return beam 108 is combined with the reference beam 105 by the optical coupler 131. Polarization controllers 153-1 to 153-4 adjust the polarization states of the measuring beam 106 and the reference beam 105. The reference beam 105 and the return beam 108 are combined and then split into wavelength components by a transmissive grating 141 and enter a line sensor 139. The line sensor 139 converts the intensity of light at each position (wavelength) to a voltage signal. A tomographic image of the subject's eye 107 is generated by using the voltage signal. The aberration of the return beam 108 (aberration measuring beam) is measured by a wavefront sensor 155 (aberration measuring unit). The spatial light modulator 159 is controlled so as to reduce the aberration and so as to obtain a good tomographic image irrespective of the diopter or the aberration of the subject's eye. The optical power adjuster 163, which characterizes the first embodiment, adjusts the optical power of the measuring beam 106 under the control of a personal computer 125.

The optical system of the first embodiment is a reflective optical system using spherical mirrors as the main components. However, the optical system may be a refractive optical system using lenses instead of the spherical mirrors. In the first embodiment, a reflective spatial light modulator is used. However, a transmissive spatial light modulator may be used.

Next, the light source 101 will be described. The light source 101 is a super luminescent diode (SLD), which is a typical low-coherence light source, having a wavelength of 830 nm and a bandwidth of 50 nm. The bandwidth is an important parameter that affects the resolution of an acquired tomographic image in the optical axis direction. Here, the light source is the SLD. However, other light sources, such as an amplified spontaneous emission (ASE) device or the like can be used, as long as low-coherence light can be emitted. Using near infrared light is appropriate for measuring an eye. A shorter wavelength is more appropriate, because the wavelength affects the horizontal resolution of an acquired tomographic image. In the first embodiment, the wavelength is 830 nm. The wavelength may be different from this in accordance with the position of the object to be measured. A beam is emitted by the light source 101, and the beam enters the optical power adjuster 163. Here, the optical power adjuster 163 is a continuously variable ND filter that is disposed on a fiber bench. The optical power adjuster 163 can control the optical powers of the measuring beam 106 and the reference beam 105 on the basis of a command from the personal computer 125. By using the variable ND filter as the optical power adjuster 163, the optical power can be precisely and linearly changed.

The optical power adjuster 163 of the present invention need not be a variable ND filter, and may be a unit (such as a switch) that can adjust the optical power of a light source. The present invention is not limited to the present embodiment, and it is sufficient that a loss in the optical power caused in each measuring can be corrected to the level of the optical power of a measuring beam that is defined in standards of safety (predetermined optical power). Here, the loss in the optical power caused in each measuring includes a loss that is caused not only due to a decrease in the diffraction efficiency of a spatial light modulator but also due to a change in the size of an aperture disposed on the light path and a change of a dioptric lens.

The loss in the optical power may be measured for each measuring and used as feedback to the optical power adjuster 163 to correct the level of the optical power to the predetermined optical power. Thus, the optical power of the measuring beam can be precisely adjusted. In this case, the optical power of the measuring beam may be measured by an optical power measuring unit disposed on the measuring light path as in the second example described below, or may be measured by an aberration measuring unit that is disposed at a position that is pupil conjugate.

In order to increase the safety for a subject's eye, a shutter may be disposed on the measuring path and the shutter may be opened when it is detected that the optical power is smaller than the predetermined optical power.

Next, the optical path of the reference beam 105 will be described. The reference beam 105, which has been split by the optical coupler 131, travels through a single-mode fiber 130-2 to a lens 135-1 that collimates the reference beam 105 into a collimated beam having a diameter of 4 mm. Next, the reference beam 105 is reflected by the mirrors 157-1 and 157-2 to a mirror 114, which is a reference mirror. The optical path length of the reference beam 105 is made substantially the same as the optical path length of the measuring beam 106, so that the reference beam 105 can interfere with the measuring beam 106. Next, the reference beam 105 is reflected by the mirror 114, and guided again to the optical coupler 131. The reference beam 105 passes through a dispersion compensation glass 115 that compensates the reference beam 105 for the dispersion that is generated while the measuring beam 106 travels to and returns from the subject's eye 107. The dispersion compensation glass 115 has a length L1. Here, L1=23 mm, which corresponds to the diameter of an eyeball of an average Japanese person. An electric stage 117-1 can move in a direction indicated by an arrow so as to adjust the optical path length of the reference beam 105. The electric stage 117-1 is driven under the control of the personal computer 125.

Next, the optical path of the measuring beam 106, which characterizes the first embodiment, will be described. The measuring beam 106, which has been split by the optical coupler 131, is guided through the optical fiber 130-4 to a lens 135-4 that collimates the measuring beam 106 into a collimated beam having a diameter of 4 mm. The polarization controller 153-1 or 153-4 can adjust the polarization state of the measuring beam 106. Here, the measuring beam 106 and the reference beam 105 are linear polarized light that is parallel to the paper surface. The measuring beam 106 passes through a beam splitter 158, is reflected by the spherical mirrors 160-1 and 160-2, enters the spatial light modulator 159, and is modulated by the spatial light modulator 159. The spatial light modulator 159 is oriented so as to modulate the phase of a linearly polarized beam that is parallel to the paper surface (p-polarized light), which is aligned with the polarization of the measuring beam 106. Here, an LCOS spatial light modulator (X10468-02) made by Hamamatsu Photonics K.K. is used as the spatial light modulator 159. The measuring beam 106 is reflected by the spherical mirrors 160-3 and 160-4 and impinges on a mirror of the XY scanner 119. For simplicity, the XY scanner 119 is illustrated as a mirror. In practice, however, an X-scanning mirror and a Y-scanning mirror are disposed adjacent to each other so as to raster scan a retina 127 in a direction perpendicular to the optical axis. The center of the measuring beam 106 is aligned with the center of the rotation center of the mirror of the XY scanner 119. The spherical mirrors 160-5 to 160-7, which serve as an optical system for scanning the retina 127, make the measuring beam 106 scan the retina 127 with a point near a cornea 126 as a fulcrum.

Here, the beam diameter of the measuring beam 106 is 4 mm. In order to acquire a tomographic image having a higher resolution, the beam diameter may be larger. Due to safety standards, the optical power of the measuring beam 106 is adjusted to 700 µW by using the optical power adjuster 163. The adjustment method will be described below. An electric stage 117-2 can move in a direction indicated by an arrow so as to adjust and control the position of the spherical mirror 160-6 attached thereto. By adjusting the position of the spherical mirror 160-6, the measuring beam 106 can be focused on a predetermined layer of the retina 127 of the subject's eye 107 so as to observe the layer. In the initial state, the position of the spherical mirror 160-2 is adjusted so that the measuring beam 106 enters the cornea 126 as a collimated beam. Even when the subject's eye 107 has ametropia, the subject's eye can be observed. After entering the subject's eye 107, the measuring beam 106 is reflected or scattered by the retina 127 to become the return beam 108, is guided again to the optical coupler 131, and reaches the line sensor 139.

A part of the return beam 108, which is split from the return beam 108 by the beam splitter 158, enters the wavefront sensor 155, which measures the aberration of the return beam 108. The wavefront sensor 155 is electrically connected to the personal computer 125. Here, the spherical mirrors 160-1 to 160-7 are disposed so that the cornea 126, the XY scanner 119, the wavefront sensor 155, and the spatial light modulator 159 are optically conjugate to each other. Therefore, the wavefront sensor 155 can measure the aberration of the subject's eye 107. Moreover, the spatial light modulator 159 can correct the aberration due to the subject's eye 107. Furthermore, the spatial light modulator 159 is controlled in real time on the basis of the aberration obtained, so that the aberration generated in the subject's eye 107 is corrected and a tomographic image having a higher horizontal resolution can be acquired.

Instead of the spherical mirror 160-6 used here, a cylindrical mirror may be used depending on the aberration (ametropia) of the subject's eye 107. An additional lens may be disposed on the optical path of the measuring beam 106. Here, the wavefront sensor 155 measures the aberration by using the measuring beam 106. However, the aberration may be measured by using an aberration measuring beam that is emitted by another light source. An additional optical path may be made in order to measure the aberration. For example, a beam splitter may be disposed between the spherical mirror 160-7 and the cornea 126 so as to generate a beam for measuring the aberration.

Next, the structure of the measurement system of the OCT apparatus according to the first embodiment will be described. The OCT apparatus 100 can acquire a tomographic image (OCT image) that is formed of the intensity of an interference signal measured by a Michelson interferometer system. In the measurement system, the return beam 108, which has been reflected or scattered by the retina 127, is combined with the reference beam 105 by the optical coupler 131 to generate a combined beam 142. The combined beam 142 travels through an optical fiber 130-3 and a lens 135-2 and enters the transmissive grating 141. The combined beam 142 is split into wavelength components by the transmissive grating 141, focused by a lens 135-3, and the line sensor 139 converts the intensity of the combined beam at each position (wavelength) to a voltage. To be specific, an interference pattern of spectral regions on the wavelength axis is observed on the line sensor 139.

The voltage signals that have been acquired by the line sensor 139 are converted to digital data by a frame grabber 140. The personal computer 125 performs data processing and generates a tomographic image. Here, the line sensor 139 has 1024 pixels and can acquire the intensity of each of the wavelengths (1024 wavelength segments) of the combined beam 142. A part of the return beam 108, which is split by the beam splitter 158, enters the wavefront sensor 155, and the aberration of the return beam 108 is measured. The wavefront sensor 155 is a Shack-Hartmann wavefront sensor. The aberration is represented by using a Zernike polynomial, which represents the aberration of the subject's eye 107. The Zernike polynomial includes tilt terms, defocus terms, astigmatism terms, coma terms, trefoil terms, etc. The personal computer 125 stores a database of the optical power loss of the spatial light modulator 159. This will be described below in detail.

Figure 2A:
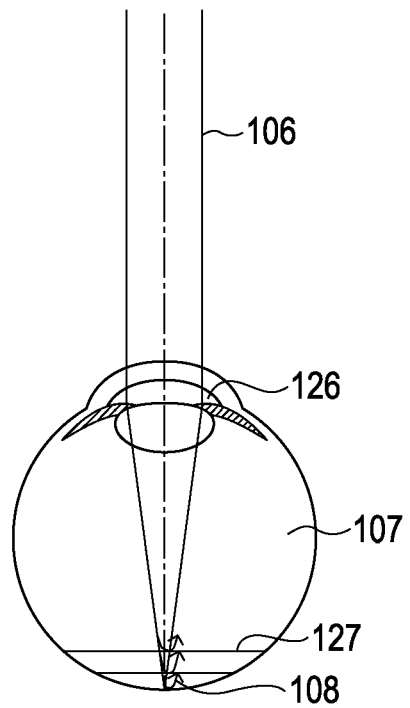
FIGS. 2A to 2C illustrate a method of acquiring a tomographic image by using the OCT apparatus according to the first embodiment of the present invention.
Figure 2B:
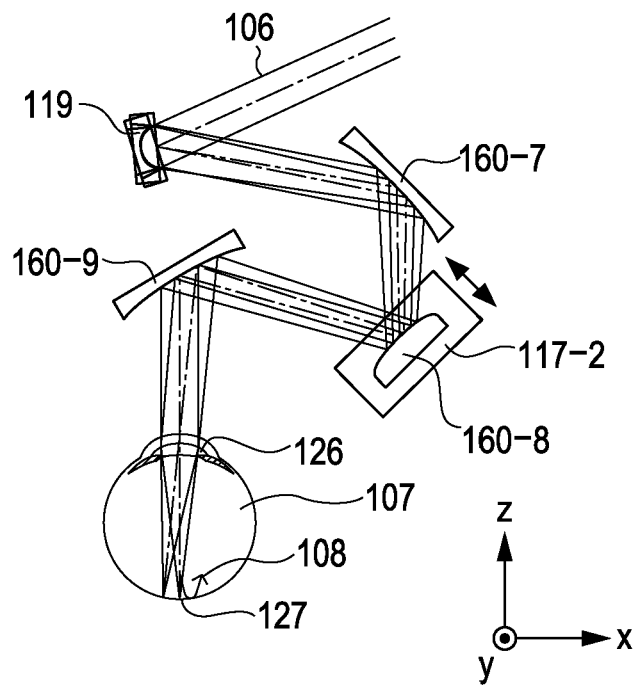
Figure 2C:
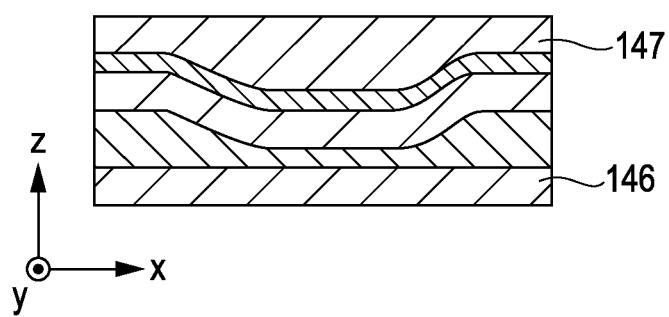

Next, a method of acquiring a tomographic image by using the OCT apparatus will be described. The OCT apparatus 100 can acquire a tomographic image of the retina 127 by controlling the XY scanner 119 and acquiring an interference pattern with the line sensor 139 (FIG. 1). Referring to FIGS. 2A to 2C, a method of acquiring a tomographic image (in a plane parallel to the optical axis) of the retina 127 will be described. FIG. 2A is a schematic view of the subject's eye 107, which is being observed by the OCT apparatus 100. As illustrated in FIG. 2A, the measuring beam 106 passes through the cornea 126 and enters the retina 127. In the retina 127, the measuring beam 106 is reflected and scattered at various positions and becomes the return beam 108. The return beam 108, which has been delayed at the various positions, reaches the line sensor 139. Here, the light source 101 has a wide bandwidth and a short coherence length. Therefore, the line sensor 139 can detect an interference pattern in the case where the optical path length of the reference optical path is substantially equal to the optical path length of the measuring optical path. As described above, the line sensor 139 acquires an interference pattern of spectral regions on the wavelength axis. Next, the interference pattern, which is the information along the wavelength axis, is converted to an interference pattern on an optical frequency axis with consideration of the characteristics of the line sensor 139 and the transmissive grating 141. The interference pattern on the optical frequency axis is inverse Fourier transformed to acquire the information in the depth direction.

As illustrated in FIG. 2B, by detecting the interference pattern while driving the X-axis of the XY scanner 119, the interference pattern for each position on the X-axis is acquired, i.e., the brightness information in the depth direction for each position on the X-axis can be acquired. As a result, a two-dimensional distribution of the intensity of the return beam 108 in the XZ-plane, which is a tomographic image 132 (FIG. 2C), is acquired. In practice, the tomographic image 132 is the arrayed intensities of the return beam 108, and displayed, for example, by representing the intensities in gray scale. Here, only the boundaries of the acquired tomographic image are illustrated. A pigmented layer 146 and an optic nerve fiber layer 147 of the retina are illustrated.

Figure 3A:
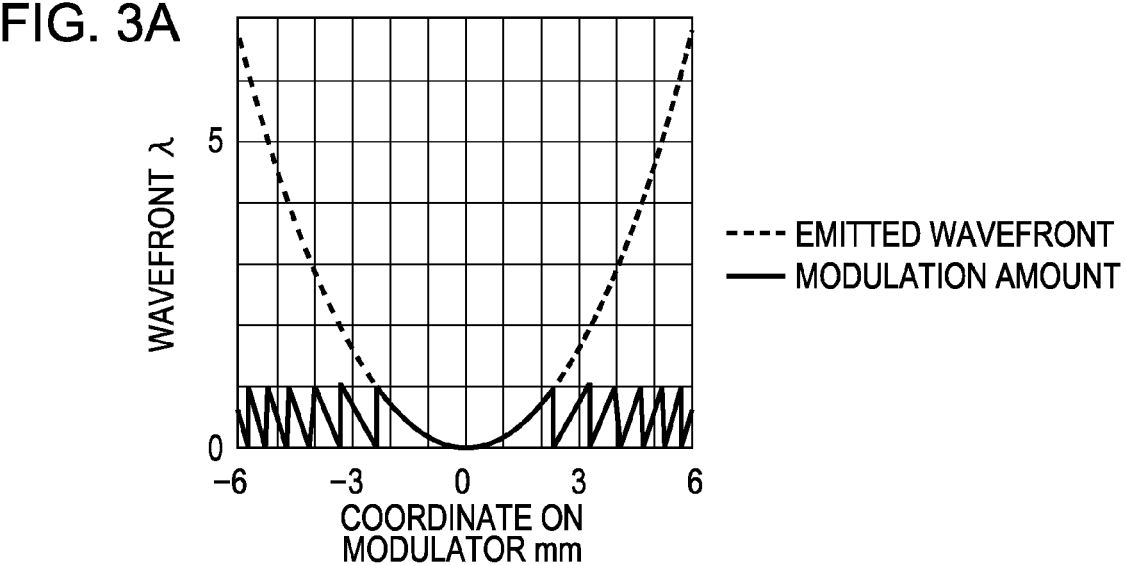
FIGS. 3A to 3C illustrate a method of controlling the optical power of the measuring beam of the OCT apparatus according to the first embodiment of the present invention.
Figure 3B:
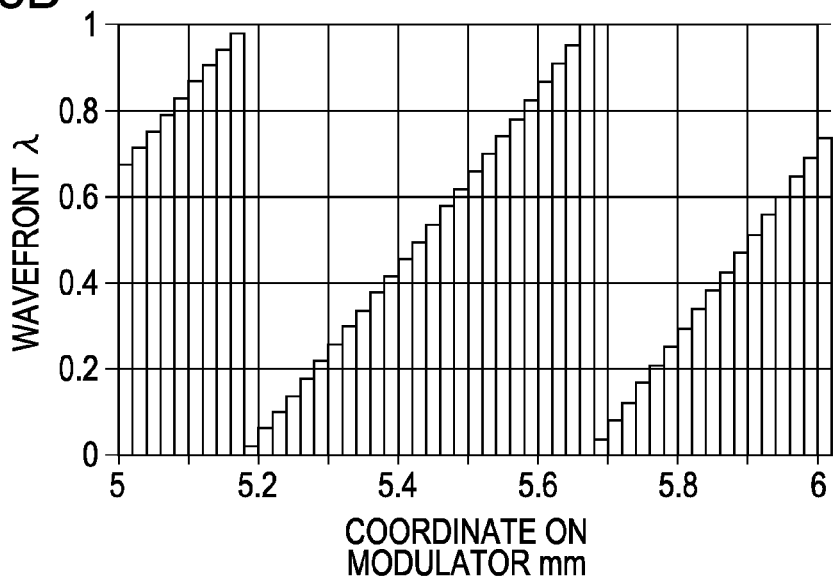
Figure 3C:
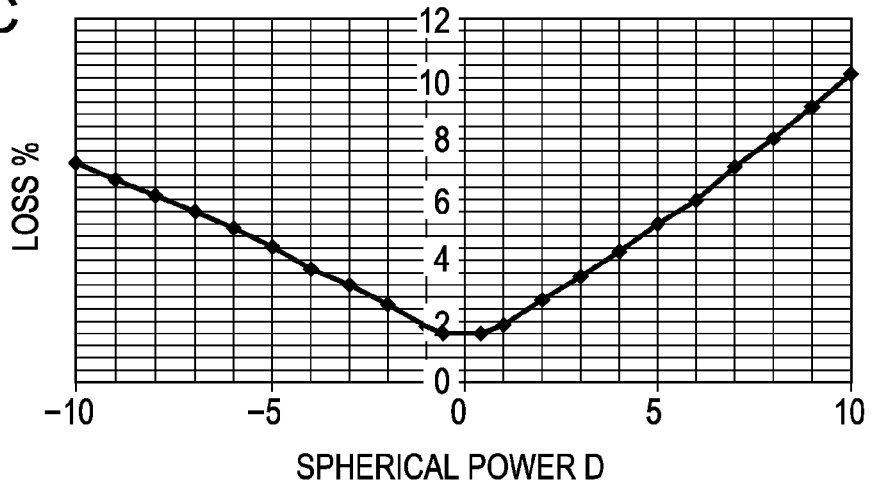

Referring to FIGS. 3A to 3C, a method of controlling the optical power of the measuring beam, which characterizes the first embodiment, will be described. Here, it is assumed that the subject's eye 107 has ametropia with a spherical power of −3 D and the measuring beam 106 is focused on the retina 127 through an entrance pupil having a diameter of 4 mm. The spatial light modulator 159, which is an LCOS spatial light modulator (X10468-02) made by Hamamatsu Photonics K.K., has a modulation surface of 12 mm×12 mm, a pixel size of 20 μm×20 μm, and the number of pixels used 600×600. In FIG. 3A, the wavefront of the measuring beam 106 to be emitted from the modulation surface of the spatial light modulator 159 is shown by a broken line. The maximum modulation amount of the spatial light modulator 159 is λ. Because it is impossible to directly generate the wavefront shown by the broken line, the wavefront is generated by using phase wrapping. In FIG. 3A, the modulation amount for generating the wavefront shown by the broken line by using phase wrapping is shown by a solid line. The horizontal axis represents the coordinate on the modulator, and the vertical axis represents the wavefront (the positive direction representing a delay in the phase). FIG. 3B illustrates the details of the modulation amount for the coordinate of 5 to 6 mm on the modulator. Because the modulation is performed pixel by pixel, the modulation amount is discontinuous with respect to the coordinate. If the number of pixels included in a curved surface (here, 5.18 to 5.68 mm) is small, the diffraction efficiency of the first-order diffracted light that is used for acquiring an image is reduced. In this case, when the shape of the measuring beam (Gaussian beam) and the diffraction efficiently of the modulator (supplier's data) are multiplied, the entire modulator has 3.1% loss in the optical power. FIG. 3C illustrates the loss in the light for the spherical power in the range of +10 D to −10 D. The loss in the optical power of the spatial light modulator 159 can be calculated from at least one of the spherical power and the cylindrical power of the subject's eye 107. Here, the loss in the optical power in the spatial light modulator 159 can be calculated from the spherical power of the subject's eye 107 by using, for example, a database 165 of the relationship between the spherical power and the loss in the optical power illustrated in FIG. 3C and stored in the personal computer 125. Alternatively, the loss in the optical power may be directly calculated from the spherical power by using the personal computer 125. For example, the personal computer 125 is made to function as a modulation pattern generation and output unit that generates a modulation pattern from at least one of the spherical power and the cylindrical power of the subject's eye and outputs the modulation pattern to the spatial light modulator. By using the modulation pattern output to the spatial light modulator, the loss in the optical power when the measuring beam enters the spatial light modulator is calculated. In this caser, the modulation pattern generation and output unit may also serve as an optical power loss calculation unit that calculates the loss in the optical power. In the first embodiment, the optical power of the measuring beam 106 that enters the subject's eye 107 can be controlled in accordance with the spherical power or the cylindrical power of the subject's eye by operating the optical power adjuster 163 on the basis of the loss in the optical power that has been calculated as described above.

Next, the method of adjusting the optical power will be described. Here, it is assumed that the transmittance of the optical power adjuster 163 is adjusted to 70% and the optical power of the incident beam that enters the optical power adjuster 163 is 10 mW. If the spherical power of the subject's eye 107 is 0 D, the measuring beam 106 having a power of 700 μW enters the subject's eye 107. However, in the above case where the subject's eye 107 has ametropia of spherical power of −3 D, the optical power that enters the subject's eye 107 is 10 mW×0.7×0.1×(1−0.031)=678 μW. With consideration of the loss in the optical power in the spatial light modulator 159 and assuming that the transmittance of the optical power adjuster 163 is 0.7/(1−0.031)=72.2%, the optical power of the measuring beam 106 that enters the subject's eye 107 is 700 μW. In the first embodiment, by adjusting the optical power in this manner, the optical power of the measuring beam can be made constant irrespective of the modulation pattern of the spatial light modulator. Here, a case where the subject's eye 107 has spherical ametropia has been described. However, the first embodiment can be used when the subject's eye 107 has ametropia due to astigmatism.

Figure 4:
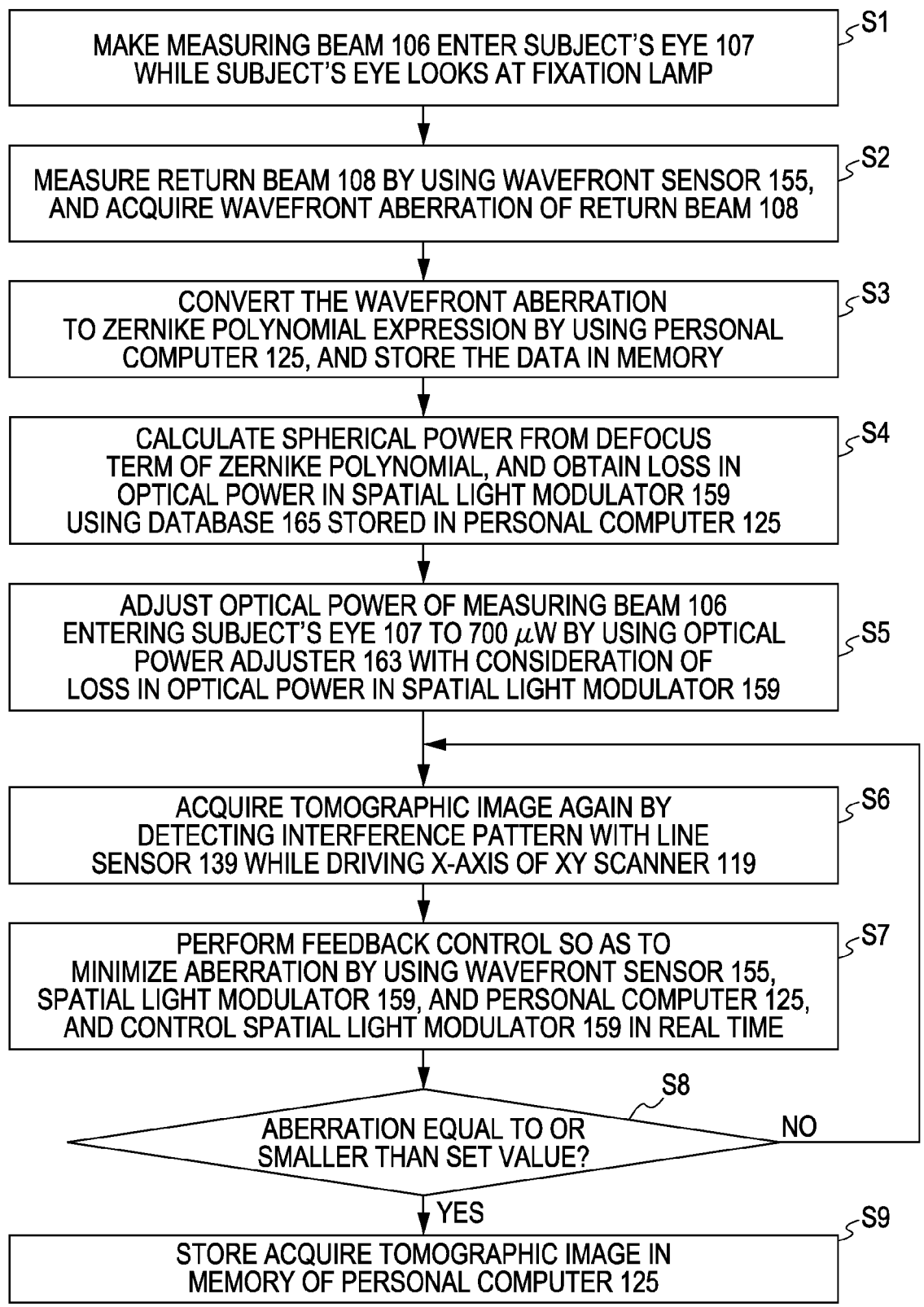
FIG. 4 is a flowchart illustrating steps of acquiring a tomographic image by using the OCT apparatus according to the first embodiment the present invention.

Referring to FIGS. 1 to 4, the steps of acquiring a tomographic image by using the OCT apparatus will be described. FIG. 4 is a flowchart illustrating the steps of acquiring a tomographic image by using the OCT apparatus 100. Here, as illustrated in FIG. 4, an aberration generated in the subject's eye 107 having myopia is corrected by using the spatial light modulator 159 so as to acquire a high-horizontal-resolution tomographic image of the retina 127. The same method can be used in the case where the subject's eye 107 has astigmatism or hyperopia. The tomographic image is acquired by performing the following steps (1) to (9). The steps may be performed sequentially or in a different order. The steps may be automatically performed by using a computer or the like. FIG. 4 is a flowchart of the process of acquiring the tomographic image.

(1) In step 1 (S1 in FIG. 4), the measuring beam 106 is made to enter the subject's eye 107 while the subject's eye 107 looks at a fixation lamp (not shown). Here, the position of the spherical mirror 160-6 is adjusted by the electric stage 117-2 so that the measuring beam 106 enters the subject's eye 107 as a collimated beam.

(2) In step 2 (S2 in FIG. 4), the return beam 108 is measured by using the wavefront sensor 155, and the aberration of the return beam 108 is acquired (3) In step 3 (S3 in FIG. 4), the acquired aberration is converted to a Zernike polynomial expression by using the personal computer 125, and the data is stored in a memory.

(4) In step 4 (S4 in FIG. 4), the spherical power is calculated from the defocus term of the polynomial, and the loss in the optical power in the spatial light modulator 159 is obtained by using the database 165 stored in the personal computer 125, which is shown in FIG. 3C.

(5) In step 5 (S5 in FIG. 4), with consideration of the loss in the optical power, the optical power of the measuring beam 106 that enters the subject's eye 107 is adjusted to 700 µW by using the optical power adjuster 163.

(6) In step 6 (S6 in FIG. 4), a tomographic image (not shown) is acquired by detecting an interference pattern with the line sensor 139 while driving the X-axis of the XY scanner 119.

(7) In step 7 (S7 in FIG. 4), while continuously performing step 6, feedback control is performed so as to minimize the aberration by using the wavefront sensor 155, the spatial light modulator 159, and the personal computer 125 so as to control the spatial light modulator 159 in real time.

(8) In step 8 (S8 in FIG. 4), whether the aberration is equal to or smaller than a set value is determined, and steps 6 to 7 are repeated until the aberration converges. The set value can be about 0.1 µm (root mean square (RMS)).

(9) In step 9 (S9 in FIG. 4), the acquired tomographic image is stored in the memory of the personal computer 125.

As described above, with the structure according to the first embodiment including the spatial light modulator that modulates at least one of the measuring beam and the return beam to correct the aberration generated in the object, and the optical power adjuster that controls the optical power of the measuring beam to compensate for the loss in the optical power when the measuring beam enters the spatial light modulator, whereby the loss in the optical power of the measuring beam in the spatial light modulator can be offset. Thus, the optical power of the measuring beam can be made constant irrespective of the modulation pattern of the spatial light modulator, so that the signal to noise ratio of the tomographic image can be increased. The spatial light modulator and the wavefront sensor are disposed optically conjugate to each other, so that the aberration can be efficiently corrected. In the case where the object is a subject's eye, the modulation pattern output to the spatial light modulator is generated from at least one of the spherical power and the cylindrical power of the subject's eye by using the personal computer, so that the modulation pattern can be generated and output by using the spherical power or the cylindrical power of the subject's eye that has been acquired by using another ophthalmological apparatus. Therefore, the modulation pattern can be optimized in a short time, so that the image can be efficiently acquired. The modulation pattern is output to the spatial light modulator and the loss in the optical power when the measuring beam enters the spatial light modulator is calculated, so that the optical power of the measuring beam that enters the subject's eye can be efficiently determined. In the case where the object is the subject's eye, the database is used to convert at least one of the spherical power and the cylindrical power of the subject's eye to the loss in the optical power that is generated when the measuring beam enters the spatial light modulator. Thus, the loss in the optical power is estimated using the spherical power and the cylindrical power, so that the optical power of the measuring beam can be efficiently controlled. The aberration of the return beam is measure, and the aberration of the subject's eye is corrected by correcting the aberration of at least one of the measuring beam and the return beam is corrected on the basis of the measured aberration. As a result, an optical imaging can be performed with a high measurement sensitivity and a high horizontal resolution. Moreover, according to the first embodiment, light emitted from the light source is split into the measuring beam and the reference beam, and by using an interference signal generated by the interference between the return beam of the measuring beam, with which the object is irradiated, and the reference beam, which has travelled through the reference optical path, an optical imaging method of acquiring a tomographic image of the object can be constructed as follows. First, in the first step, the aberration of an object is measured by using the wavefront sensor. In the second step, the modulation amount for correcting the aberration of the objet using the spatial light modulator unit is calculated, and the spatial light modulator is controlled on the basis of the calculated modulation amount. In the third step, the loss in the optical power due to the spatial light modulator is calculated by using the personal computer for calculating the loss in the optical power when the measuring beam enters the spatial light modulator. In the fourth step, the optical power of the measuring beam is adjusted so as to offset the loss in the optical power in the spatial light modulator by using the optical power adjuster for adjusting the optical power of the measuring beam on the basis of the loss in the optical power that has been calculated in the third step.

Second Embodiment

In the second embodiment, an OCT apparatus including an adaptive optics system that acquires a tomographic image (OCT image) of a subject's eye with high horizontal resolution will be described. As with the first embodiment, the second embodiment is a Fourier domain OCT apparatus that corrects the aberration of the subject's eye by using the reflective spatial light modulator and acquires a tomographic image of a subject's eye. Such an OCT apparatus can acquire a good tomographic image irrespective of the diopter or the aberration the subject's eye. In the second embodiment, an optical power measurement unit that measures the optical power of the measuring beam and an optical power adjuster that measure the optical power of the measuring beam are provided. A reflective liquid crystal spatial light modulator employing the orientation of liquid crystal is used as the spatial light modulator. As long as the spatial light modulator can modulate the phase of light, materials other than liquid crystal may be used.

Figure 5:
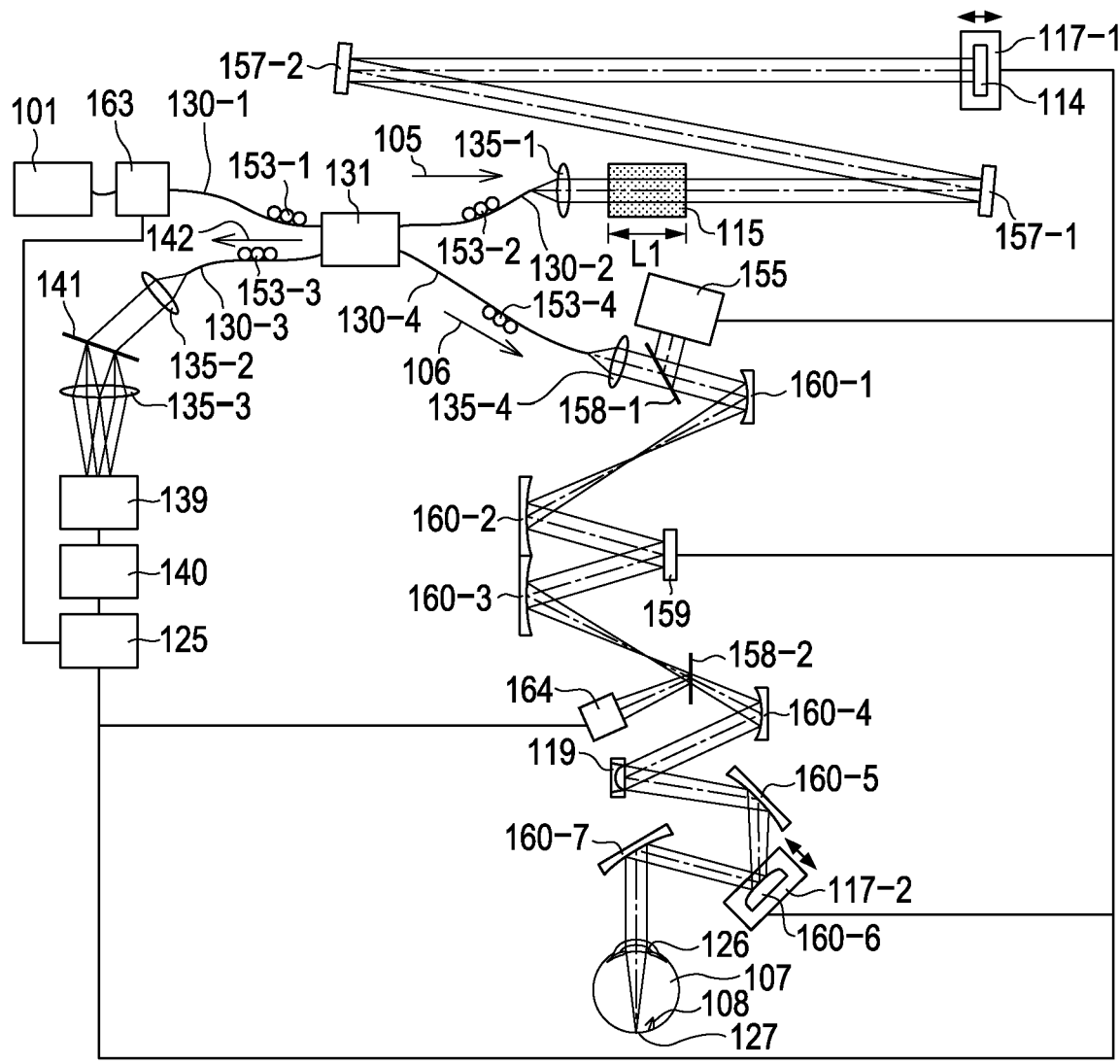
FIG. 5 illustrates the overall structure of an OCT apparatus according to a second embodiment the present invention.

Referring to FIG. 5, the overall structure of the OCT apparatus according to the second embodiment will be described. In the second embodiment, the elements the same as those of FIG. 1 denoted by the same numerals, and redundant description will be omitted. In FIG. 5, the measuring beam 106 travels through the optical fiber 130-4, the spatial light modulator 159, and the spherical mirrors 160-1 to 160-3, to a beam splitter 158-2. A optical power measurement unit 164, which characterizes the second embodiment, has a function of measuring the optical power of a part of the measuring beam 106. The description of the light source 101 and the reference optical path, which are the same as those of the first embodiment, is omitted.

Next, the optical path of the measuring beam 106, which characterizes the second embodiment, will be described. The measuring beam 106, which has been split by the optical coupler 131, is guided through the single-mode fiber 130-4 to the lens 135-4 that collimates the measuring beam 106 into a collimated beam having a diameter of 4 mm. The polarization controller 153-1 or 153-4 can adjust the polarization state of the measuring beam 106. Here, the measuring beam 106 and the reference beam 105 are linear polarized light that is parallel to the paper surface. The measuring beam 106 passes through a beam splitter 158-1, is reflected by the spherical mirrors 160-1 and 160-2, enters the spatial light modulator 159, and is modulated by the spatial light modulator 159. The spatial light modulator 159 is oriented so as to modulate the phase of a linearly polarized beam that is parallel to the paper surface (p-polarized light), which is aligned with the polarization of the measuring beam 106. Here, an LCOS spatial light modulator (X10468-02) made by Hamamatsu Photonics K.K. is used as the spatial light modulator 159.

The measuring beam 106 is reflected by the spherical mirror 160-3 and guided to the beam splitter 158-2. A part of the measuring beam 106, which is split by the beam splitter 158-2, is guide to the optical power measurement unit 164, and the optical power of the measuring beam 106 is measured by the optical power measurement unit 164. The optical power measurement unit 164 is electrically connected to the personal computer 125. The beam splitter 158-2 splits the measuring beam 106 with a ratio of 9:1, and 10% of the measuring beam 106 enters the optical power measurement unit 164. The measuring beam 106 is reflected by the spherical mirror 160-4, and impinges on the mirror of the XY scanner 119. The optical power of the measuring beam 106 is adjusted to 700 µW. The adjustment method will be described below. The description of the measurement system and the method of acquiring a tomographic image, which are the same as those of the first embodiment, is omitted.

Referring to FIGS. 3A to 5, the method of controlling the optical power of the measuring beam, which characterizes the present invention, will be described. As in the first embodiment, it is assumed that the subject's eye 107 has ametropia with a spherical power of −3 D and the measuring beam 106 is focused on the retina 127 through an entrance pupil having a diameter of 4 mm. As in the first embodiment, when the modulation amount shown by the solid line in FIG. 3A is supplied to the spatial light modulator 159, the measuring beam 106 can be focused on the retina 127. At the same time, the optical power of the measuring beam 106 can be measured by using the optical power measurement unit 164. The second embodiment differs from the first embodiment in that the optical power of the measuring beam 106 is measured so as to obtain the loss in the optical power due to the modulator. As described above, the loss in the optical power in the spatial light modulator 159 can be obtained by using the optical power measurement unit 164. Moreover, with consideration of the loss in the optical power, the optical power of the measuring beam 106 that enters the subject's eye 107 can be controlled by using the optical power adjuster 163. Here, a case where the subject's eye 107 has spherical ametropia has been described. However, the first embodiment can be used when the subject's eye 107 has ametropia due to astigmatism.

Referring to FIGS. 5 and 6, the steps of acquiring a tomographic image by using the OCT apparatus will be described. FIG. 6 is a flowchart illustrating the steps of acquiring a tomographic image by using the OCT apparatus 100. Here, as illustrated in FIG. 6, an aberration generated in the subject's eye 107 having myopia is corrected by using the spatial light modulator 159 so as to acquire a high-horizontal-resolution tomographic image of the retina 127. The same method can be used in the case where the subject's eye 107 has astigmatism or hyperopia. The tomographic image is acquired by performing the following steps (1) to (7). The steps may be performed sequentially or in a different order. The steps may be automatically performed by using a computer or the like. FIG. 6 is a flowchart of the process of acquiring the tomographic image.

(1) In step 1 (S1 in FIG. 6), the measuring beam 106 is made to enter the subject's eye 107 while the subject's eye 107 looks at a fixation lamp (not shown). Here, the position of the spherical mirror 160-6 is adjusted by the electric stage 117-2 so that the measuring beam 106 enters the subject's eye 107 as a collimated beam.

(2) In step 2 (S2 in FIG. 6), a tomographic image (not shown) is acquired by detecting an interference pattern with the line sensor 139 while driving the X-axis of the XY scanner 119.

(3) In step 3 (S3 in FIG. 6), while continuously performing step 2, feedback control is performed so as to minimize aberration by using the wavefront sensor 155, the spatial light modulator 159, and the personal computer 125 so as to control the spatial light modulator 159 in real time.

(4) In step 4 (S4 in FIG. 6), the optical power of the measuring beam 106 is measured by using the optical power measurement unit 164.

(5) In step 5 (S5 in FIG. 6), while continuously performing step 4, the optical power of the measuring beam 106 that enters the subject's eye 107 is adjusted to 700 µW by using the optical power adjuster 163.

(6) In step 6 (S6 in FIG. 6), whether the aberration is equal to or smaller than a set value is determined, and steps 2 to 5 are repeated until the aberration converges. The set value can be about 0.1 µm (RMS).

(7) In step 7 (S7 in FIG. 6), the acquired tomographic image is stored in the memory of the personal computer 125.

As described above, the second embodiment includes the optical power measurement unit that measures the optical power of the measuring beam, so that the loss in the optical power in the spatial light modulator can be obtained and the optical power of the measuring beam can be made constant irrespective of the modulation patter of the spatial light modulator. As a result, the signal to noise ratio of a tomographic image can be increased. According to the second embodiment, light from the light source is split into the measuring beam and the reference beam, and the return beam that is generated by irradiating the object with the measuring beam and the reference beam that has travelled through the reference optical path are made to interfere with each other to generate an interfere signal. By using the interference signal, an optical imaging method of acquiring a tomographic image of an object can be constructed as follows. In the first step, an aberration of the object is measured by using a wavefront sensor. In the second step, a modulation amount of correcting the aberration of the object by using the spatial light modulator is calculated, and the spatial light modulator is controlled on the basis of the calculated modulation amount. In the third step, the loss in the optical power in the spatial light modulator is calculated by using an optical power measurement unit that measures the loss in the optical power generated when the measuring beam enters the spatial light modulator. In fourth step, on the basis of the loss in the optical power calculated in the third step, the optical power the measuring beam is adjusted so as to offset the loss in the optical power in the spatial light modulation unit by using an optical power adjuster that adjusts the optical power of the measuring beam.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-251415 filed Oct. 30, 2009, which is hereby incorporated by reference herein in its entirety.

What is claimed is:

1. An adaptive optics apparatus comprising:
a light source;
a spatial light modulation unit configured to modulate the phase of light emitted by the light source;
an optical power acquiring unit configured to acquire an optical power that is loss of light in the spatial light modulation unit; and
an optical power adjusting unit configured to adjust an optical power of light emitted by the light source to a predetermined optical power in accordance with the optical power that is lost in the spatial light modulation unit.

2. The adaptive optics apparatus according to claim 1, further comprising:
an aberration measuring unit configured to measure an aberration of an object,
wherein the spatial light modulation unit modulates light via the optical power adjusting unit on the basis of a measurement result obtained by the aberration measuring unit.

3. The adaptive optics apparatus according to claim 2, wherein the optical power acquiring unit acquires the optical power that is lost in the spatial light modulation unit on the basis of a measurement result obtained by the aberration measuring unit.

4. The adaptive optics apparatus according to claim 2, wherein light that is used by the aberration measuring unit to measure the aberration and light that is used to acquire an image of the object are emitted by light sources that are different from each other.

5. The adaptive optics apparatus according to claim 1, wherein the spatial light modulation unit is disposed at a position that is optically conjugate to an anterior ocular segment of a subject's eye.

6. The adaptive optics apparatus according to claim 1, further comprising:
an optical power measuring unit configured to measure an optical power of light with which an object is irradiated,
wherein the optical power acquiring unit acquires the optical power that is lost in the spatial light modulation unit in accordance with a measurement result obtained by the optical power measuring unit.

7. The adaptive optics apparatus according to claim 6, further comprising:
a detection unit configured to detect whether an optical power measured by the optical power measuring unit is smaller than the predetermined optical power;
a shutter disposed on an optical path of the light emitted by the light source with which the object is irradiated; and
a control unit configured to open the shutter in accordance with a detection result obtained by the detection unit.

8. An imaging apparatus comprising:
the adaptive optics apparatus according to claim 1;
an irradiation unit configured to irradiate an object with the light that is adjusted by the optical power adjusting unit; and
an image acquiring unit configured to acquire an image of the object on the basis of a return beam returning from the object that is irradiated with light by the irradiation unit.

9. The imaging apparatus according to claim 8, further comprising:
a splitting unit configured to split the light emitted by the light source into a beam that enters the spatial light modulation unit and a reference beam,
wherein the imaging acquiring unit acquires a tomographic image of the object on the basis of an interference beam that is generated by interference between the return beam and the reference beam, the return beam returning from the object that is irradiated with light by the irradiation unit.

10. The adaptive optics apparatus according to claim 1, further comprising:
a shutter disposed on an optical path of the light emitted by the light source with which the object is irradiated; and
a control unit configured to control the shutter so that the optical power adjusting unit closes the shutter to adjust the optical power and that the shutter is opened in a case where the acquired optical power is smaller than the predetermined optical power after the optical adjusting unit adjusts the optical power.

11. A method for an adaptive optics apparatus having a light source, the method comprising:
acquiring an optical power that is loss of light in a spatial modulation unit, wherein the spatial light modulation unit modulates the phase of light emitted by the light source; and
adjusting an optical power of light emitted by the light source to a predetermined optical power in according to the optical power that is lost in the spatial light modulation unit.

12. The method according to claim 11, further comprising:
controlling a shutter so that the shutter is closed to adjust the optical power and that the shutter is opened in a case where the acquired optical power is smaller than the predetermined optical power after the optical power is adjusted.

13. A non-transitory computer-readable storage medium storing a program for causing a computer to execute a method for an adaptive optics apparatus having a light source, the method comprising:
acquiring an optical power that is loss of light in a spatial light modulation unit, wherein the spatial modulation unit modulates the phase of light emitted by the light source; and
adjusting an optical power of light emitted by the light source to a predetermined optical power in accordance with the optical power that is lost in the spatial light modulation unit.

* * * * *